United States Patent
Liu et al.

(10) Patent No.: US 10,338,047 B2
(45) Date of Patent: Jul. 2, 2019

(54) AIR-POLLUTION ANOMALY LOCATION MECHANISM

(71) Applicant: International Business Machines Corporation, Armonk, NY (US)

(72) Inventors: Liang Liu, Beijing (CN); Junmei Qu, Beijing (CN); Wen J. Yin, Beijing (CN); Chao Q. Zhu, Beijing (CN); Wei Zhuang, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 316 days.

(21) Appl. No.: 14/740,713

(22) Filed: Jun. 16, 2015

(65) Prior Publication Data
US 2016/0370339 A1    Dec. 22, 2016

(51) Int. Cl.
G01N 33/00    (2006.01)

(52) U.S. Cl.
CPC ................................ *G01N 33/0075* (2013.01)

(58) Field of Classification Search
CPC ................................................. G01N 33/0075
(Continued)

(56) References Cited

U.S. PATENT DOCUMENTS

| 8,666,666 B2 | 3/2014 | Bassa | |
|---|---|---|---|
| 2002/0146350 A1* | 10/2002 | Lo | G01N 30/02 422/89 |

(Continued)

FOREIGN PATENT DOCUMENTS

| CN | 101542266 A | 9/2009 |
|---|---|---|
| CN | 203241398 U | 10/2013 |

(Continued)

OTHER PUBLICATIONS

Shan, Nan et al., "RS and GIS Based Temporal-spatial Variation and Multi-factor Spatial Analysis on Nonpoint Source Pollution", 18th International Conference on Geoinformatics, Jun. 18-20, 2010, 4 pages.

(Continued)

*Primary Examiner* — Marc Anthony Armand
(74) *Attorney, Agent, or Firm* — Francis Lammes; Stephen J. Walder, Jr.; Grant Johnson

(57) ABSTRACT

A mechanism is provided for detecting air-pollution anomalies. A historical air-pollution pattern is identified for each of a plurality of air-pollution monitoring stations. For each of the plurality of air-pollution monitoring stations, responsive to receiving real-time data from a particular air-pollution monitoring station, the real-time data is compared to the historical air-pollution pattern associated with the particular air-pollution monitoring station. A density difference value is generated based on the comparison of the real-time data to the historical air-pollution pattern associated with the particular air-pollution monitoring station and a determination is made as to whether the density difference value is greater than a predetermined confidence threshold. For each of a subset of the plurality of air-pollution monitoring stations whose associated density difference value is greater than the predetermined confidence threshold, an indication of an anomaly in detected air-pollution levels is identified to an administrator.

20 Claims, 5 Drawing Sheets

(58) Field of Classification Search
USPC .......................................................... 702/183
See application file for complete search history.

(56) References Cited

U.S. PATENT DOCUMENTS

| | | | | |
|---|---|---|---|---|
| 2009/0265037 | A1* | 10/2009 | Bassa | B60H 1/00771 |
| | | | | 700/276 |
| 2009/0309744 | A1* | 12/2009 | Fu | G01C 21/3461 |
| | | | | 340/632 |
| 2012/0297028 | A1 | 11/2012 | Das et al. | |
| 2015/0077737 | A1* | 3/2015 | Belinsky | G01N 15/0211 |
| | | | | 356/51 |
| 2016/0125307 | A1* | 5/2016 | Zheng | G06N 3/08 |
| | | | | 706/12 |

FOREIGN PATENT DOCUMENTS

| | | | | |
|---|---|---|---|---|
| CN | 103595792 | A | | 2/2014 |
| CN | 103616732 | A | | 3/2014 |
| KR | 20090098127 | | * 9/2009 ............. G06Q 50/26 |
| TW | 200951888 | A | | 12/2009 |
| WO | WO 2013/150349 | A1 | | 10/2013 |
| WO | WO 2014/194480 | A1 | | 12/2014 |

OTHER PUBLICATIONS

Song, Shujun, "A GIS-Based Approach to Spatio-Temporal Analysis of Urban Air Quality in Chengdu Plain", The International Archives of the Photogrammetry, Remote Sensing and Spatial Information Sciences, vol. XXXVII, Part B7, http://www.isprs.org/proceedings/XXXVII/congress/7_pdf/9_ThS-17/08.pdf, Beijing, China, 2008 (month unknown), pp. 1447-1450.

* cited by examiner

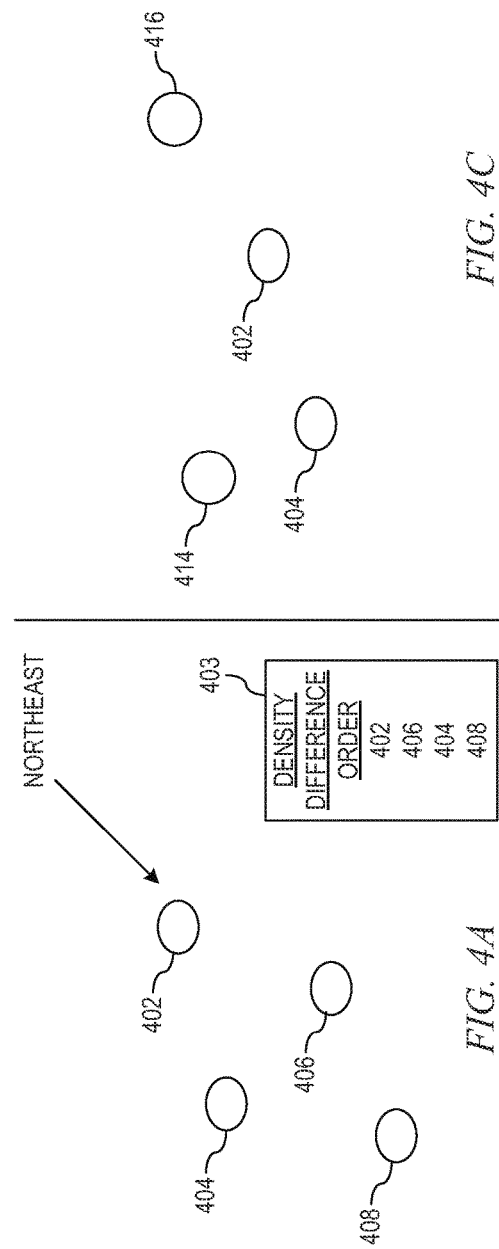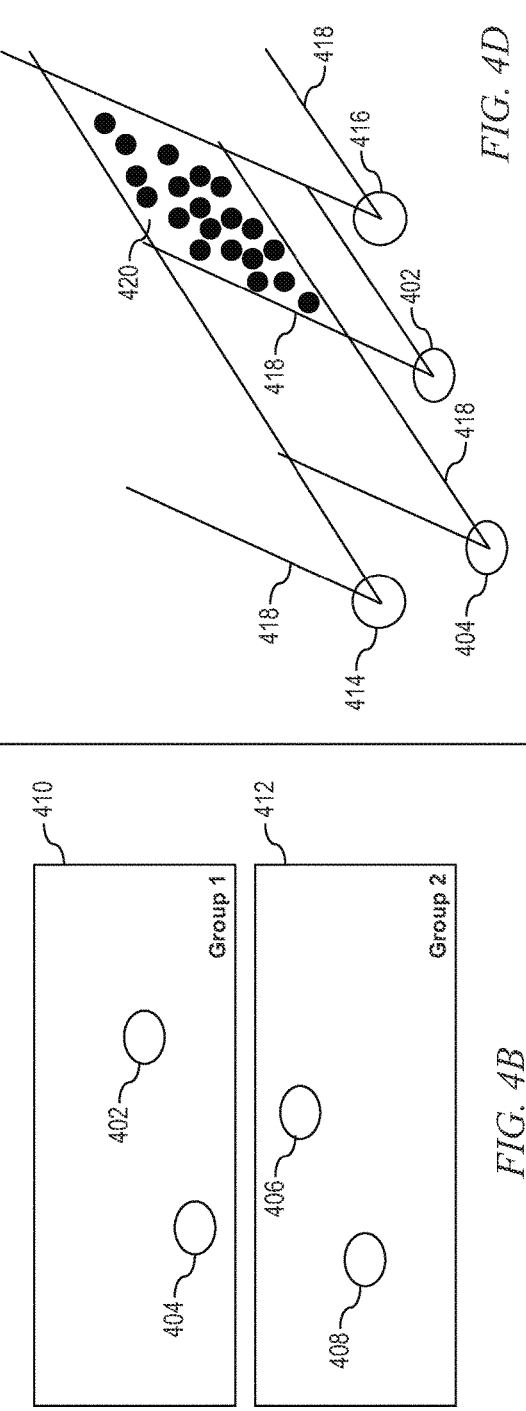

AIR-POLLUTION ANOMALY LOCATION MECHANISM

BACKGROUND

The present application relates generally to an improved data processing apparatus and method and more specifically to mechanisms for locating air-pollution anomalies utilizing air quality monitoring stations.

Air pollution is an introduction of particulates, biological molecules, or other harmful materials into Earth's atmosphere, causing disease, death to humans, damage to other living organisms such as food crops, or the natural or built environment. Air pollution may come from anthropogenic, i.e. an effect or object resulting from human activity, or natural sources. Some of the main anthropogenic sources include: traffic, coal-burning, industry production, and dust emission.

The Earth's atmosphere is a complex natural gaseous system that is essential to support life on planet Earth. Stratospheric ozone depletion due to air pollution has been recognized as a threat to human health as well as to the Earth's ecosystems. Some of the current control measures to control the anthropogenic forms of air pollution include: traffic control, industry production restrictions or limits, and technology improvements.

SUMMARY

In one illustrative embodiment, a method, in a data processing system, is provided for detecting air-pollution anomalies. The illustrative embodiment identifies a historical air-pollution pattern for each of a plurality of air-pollution monitoring stations. For each of the plurality of air-pollution monitoring stations: the illustrative embodiment compares the real-time data to the historical air-pollution pattern associated with the particular air-pollution monitoring station in response to receiving real-time data from a particular air-pollution monitoring station; generates a density difference value based on the comparison of the real-time data to the historical air-pollution pattern associated with the particular air-pollution monitoring station; and determines whether the density difference value is greater than a predetermined confidence threshold. For each of a subset of the plurality of air-pollution monitoring stations whose associated density difference value is greater than the predetermined confidence threshold, the illustrative embodiment generates an indication of an anomaly in detected air-pollution levels to an administrator. In the illustrative embodiment, the indication to the administrator causes the administrator to perform one or more actions to remedy the anomaly in the detected air-pollution levels.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIGS. 4A-4D depict an illustration of identifying a location of an air-pollution anomaly in accordance with an illustrative embodiment;

DETAILED DESCRIPTION

Figure 1:
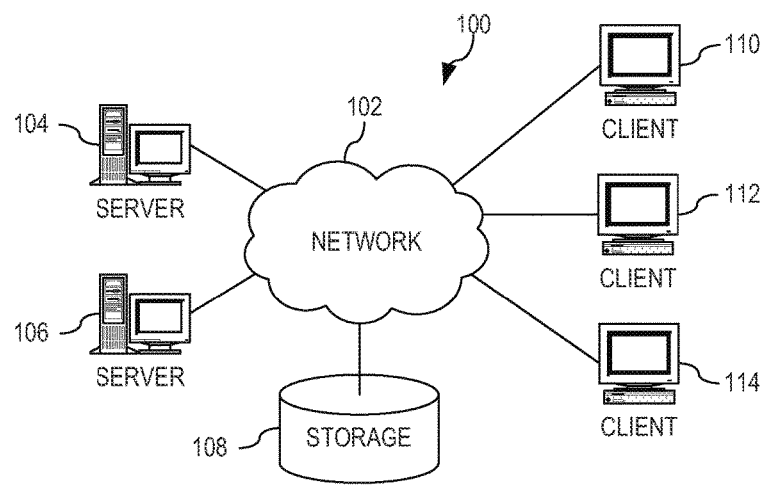
FIG. 1 is an example diagram of a distributed data processing system in which aspects of the illustrative embodiments may be implemented.

In order to better control air pollution, it is critical to identify one or more sources of the air pollution. While many industries are self-monitoring their production of air pollution, the air-pollution monitoring equipment is very expensive not only to install but to maintain. Therefore, such air-pollution monitoring equipment often goes uninstalled, unmonitored, or unrepaired, and thus serious air-pollution violations occur. The illustrative embodiments provide mechanisms that utilize a plurality of air-pollution monitoring stations in and/or around the sources of air pollution to detect air-pollution anomalies by comparing real-time monitoring data with analyzed temporal and spatial characteristics associated with the air-pollution monitoring stations. The mechanisms detect potential air-pollution anomalies by analyzing air-pollution temporal and spatial characteristics and then locating potential air-pollution anomalies according to weather conditions and correlations among nearby air-pollution monitoring stations.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 2:
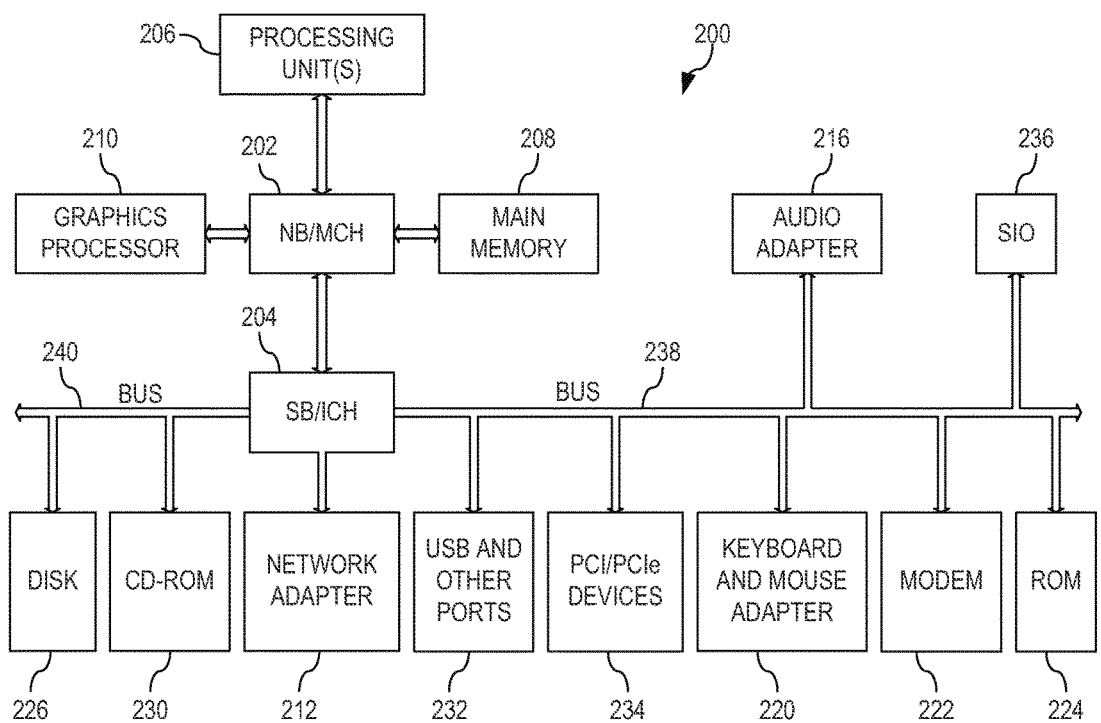
FIG. 2 is an example block diagram of a computing device in which aspects of the illustrative embodiments may be implemented.

Thus, the illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational, and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

FIG. 2 is a block diagram of an example data processing system in which aspects of the illustrative embodiments may be implemented. Data processing system 200 is an example of a computer, such as client 110 in FIG. 1, in which computer usable code or instructions implementing the processes for illustrative embodiments of the present invention may be located.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System P® computer system, Power™ processor based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
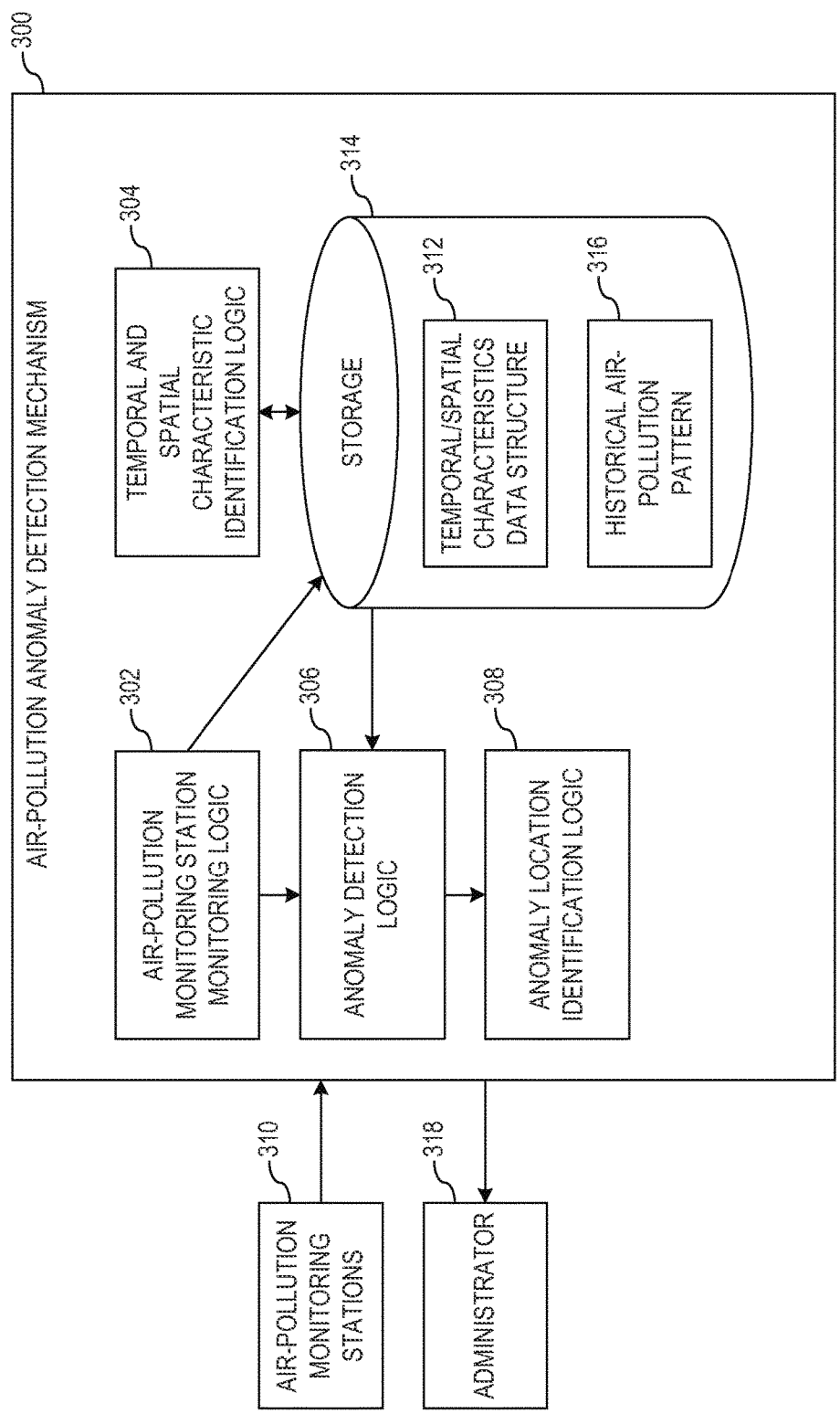
FIG. 3 depicts an air-pollution anomaly detection mechanism in accordance with an illustrative embodiment.

FIG. 3 depicts an air-pollution anomaly detection mechanism in accordance with an illustrative embodiment. Air-pollution anomaly detection mechanism 300 comprises air-pollution monitoring station monitoring logic 302, temporal and spatial characteristic identification logic 304, anomaly detection logic 306, and anomaly location identification logic 308. In order to detect air-pollution anomalies, air-pollution anomaly detection mechanism 300 initially identifies temporal and spatial characteristics associated with each of a plurality of air-pollution monitoring stations 310. In order to perform this identification, air-pollution monitoring station monitoring logic 302 monitors each of the plurality of air-pollution monitoring stations 310 receiving real-time air-pollution data regarding the level of air pollution sensed by each monitoring station in the plurality of air-pollution monitoring stations 310. Using the real-time air-pollution data, air-pollution monitoring station monitoring logic 302 calculates a pollution level variation between each of two adjacent time slots. For example, if at time $t_1$ an air-pollution monitoring station 310 detects an air-pollution level of 3 and at time $t_2$ the same air-pollution monitoring station 310 detects an air-pollution level of 4, then air-pollution monitoring station monitoring logic 302 would calculate a temporal air-pollution level variation for the air-pollution monitoring station 310 of positive 1 (+1). Air-pollution monitoring station monitoring logic 302 stores the air-pollution level variation as a temporal change for the associated air-pollution monitoring station 310 in temporal/spatial characteristics data structure 312 in storage 314.

Additionally, air-pollution monitoring station monitoring logic 302 uses the real-time air-pollution data to calculate an air-pollution level variation between each air-pollution monitoring station 310 and one or more of the remaining ones of the plurality of air-pollution monitoring stations 310 within a predetermined distance of the air-pollution monitoring station 310. For example, if at time $t_1$ an air-pollution monitoring station 310 detects an air-pollution level of 4 and, at the same time $t_1$, another air-pollution monitoring station 310 detects an air-pollution level of 3, then air-pollution monitoring station monitoring logic 302 would calculate a spatial air-pollution level variation of negative 1 (−1). The same exemplary process would be performed for each of the other remaining one of the plurality of air-pollution monitoring stations 310 associated with the current air-pollution monitoring station 310. Air-pollution monitoring station monitoring logic 302 stores the pollution level variation(s) as a spatial change for the associated air-pollution monitoring station 310 in temporal/spatial characteristics data structure 312 in storage 314.

Once initial temporal and spatial change data has been collected for air-pollution monitoring stations 310, temporal and spatial characteristic identification logic 304 analyzes the temporal change data and the spatial change data in order to identify historical temporal/spatial characteristics, i.e. a historical air-pollution pattern 316, for each of the plurality of air-pollution monitoring stations 310. That is, temporal and spatial characteristic identification logic 304 utilizes the temporal change data to generate the historical air-pollution pattern 316 for each of the plurality of air-pollution monitoring stations that shows changes in air-pollution levels over a given time period, such as a day, a week, a month, or the like. Further, using the spatial change data, temporal and spatial characteristic identification logic 304 generates the historical air-pollution pattern 316 for each of the plurality of air-pollution monitoring stations that shows changes in air-pollution levels of each of the air-pollution monitoring stations 310 at different time periods. Additionally, temporal and spatial characteristic identification logic 304 may, at periodic intervals, analyze the historical temporal/spatial change data in relation to any newly collected temporal/spatial change data in order to update the historical air-pollution pattern 316 for each of the plurality of air-pollution monitoring stations 310.

In order to detect anomalies in air-pollution levels sensed by a particular air-pollution monitoring station 310, for each of the plurality of air-pollution monitoring stations 310, anomaly detection logic 306 compares real-time air-pollution data received from the air-pollution monitoring station 310 for a given time to the temporal and spatial characteristics identified in the historical air-pollution pattern 316 for the associated air-pollution monitoring station 310 at the same time. Utilizing the comparison, anomaly detection logic 306 generates a density difference that indicates a change in air-pollution identified by the air-pollution monitoring station 310. Anomaly detection logic 306 then determines whether the density difference is larger than a predetermined confidence threshold. If the density difference exceeds the predetermined confidence threshold, then anomaly detection logic 306 provides an indication of a potential air-pollution anomaly in the detected air-pollution level to an administrator 318. Using the indication, the administrator 318 may investigate the potential air-pollution anomaly and, if there is an increase in air-pollution, take steps to decrease the air-pollution level, such as notifying a governmental agency of the violation, notifying a business (violator) that may be the cause of the air-pollution violation, or the like, which are real-world actions that may be taken when detecting an air-pollution anomaly.

In order to assist the administrator 318 in identifying a potential violator, anomaly location identification logic 308 places the air-pollution monitoring stations 310 that detected the air-pollution anomaly, i.e. anomaly detecting air-pollution monitoring station(s), above the predetermined confidence threshold in order according to the determined density difference. Utilizing obtained wind direction data, anomaly location identification logic 308 groups the anomaly detecting air-pollution monitoring stations 310 into groups based on wind direction. That is, as an example, for each of the anomaly detecting air-pollution monitoring stations 402-408 as is illustrated in FIG. 4A, if the wind is coming from the Northeast, then for each of the anomaly detecting air-pollution monitoring stations, if the anomaly detecting air-pollution monitoring station is the first anomaly detecting air-pollution monitoring station in the order according to the determined density difference 403 and if the anomaly detecting air-pollution anomaly station is also the nearest one to the Northeast, then anomaly location identification logic 308 places the anomaly detecting air-pollution monitoring station into a first group. For example, as is illustrated in FIG. 4B, anomaly detecting air-pollution monitoring station 402 in FIG. 4A is the nearest one to upwind and is also the first one in the order according to density variation, thus anomaly location identification logic 308 places anomaly detecting air-pollution monitoring station 402 in one group 1.

Otherwise, if the anomaly detecting air-pollution monitoring station is the first or next anomaly detecting air-pollution monitoring station in the order but is not the nearest one to the Northeast, then anomaly location identification logic 308 places the anomaly detecting air-pollution monitoring station into another group. Therefore, in the example, after anomaly detecting air-pollution monitoring station 402 is placed into group 1, then the next anomaly detecting air-pollution monitoring station 406 in the rest of anomaly detecting air-pollution monitoring stations which are not in groups, is the first/next anomaly detecting air-pollution monitoring station in the order according to density variation but is not the nearest to upwind (anomaly detecting air-pollution monitoring station 404 is more near to upwind). Thus, anomaly location identification logic 308 places anomaly detecting air-pollution monitoring station 406 in group 2. Anomaly location identification logic 308 repeats the operation until each of the anomaly detecting air-pollution monitoring stations is placed into a group. In continuing with the example, anomaly location identification logic 308 identifies anomaly detecting air-pollution monitoring station 404 next in the order according to density variation and is also the second nearest to upwind, thus anomaly location identification logic 308 places anomaly detecting air-pollution monitoring station 404 in group 1. Finally, anomaly detecting air-pollution monitoring station 408 is the last in the order according to density variation and is the furthest downwind, so anomaly location identification logic 308 places anomaly detecting air-pollution monitoring station 408 in group 2. Accordingly, the anomaly detecting air-pollution monitoring stations are in the order according to the density difference and also in the order according to their distances to the upwind.

Within each group of anomaly detecting air-pollution monitoring stations 410 and 412, anomaly location identification logic 308 then locates anomaly positions by calculating the influence area cross domain of nearby anomaly detecting air-pollution monitoring stations in the same group. That is, anomaly location identification logic 308 identifies one or more nearest, based on distance, non-anomaly detecting air-pollution monitoring stations 414 and 416 to each of the anomaly detecting air-pollution monitoring stations 402 and 404, as is illustrated in FIG. 4C. Anomaly location identification logic 308 then identifies an influence area 418, as is illustrated in FIG. 4D, associated with the one or more nearest non-anomaly detecting air-pollution monitoring stations 414 and 416 and the anomaly detecting air-pollution monitoring stations 402 and 404. The influence area is a triangle shaped area (two-dimensions, as shown) or a cone shaped area (three-dimensions, not shown) originating from each anomaly detecting air-pollution monitoring station and opening up in the direction of the current wind direction. Thus, in keeping with the example above, each influence area would start at the one or more nearest non-anomaly detecting air-pollution monitoring stations 414 and 416 and the anomaly detecting air-pollution monitoring stations 402 and 404 and open up to the Northeast. Anomaly location identification logic 308 then identifies a cross domain 420 of the influence areas 418 that provides an identity of the potential anomaly area, as is illustrated in FIG. 4D.

Anomaly location identification logic 308 provides an indication of the potential anomaly area to the administrator 318. Using the potential anomaly area, the administrator 318 may investigate the potential anomaly in the potential anomaly area and, if there is an increase in air-pollution may utilize the potential anomaly area to take steps to decrease the air-pollution level in that potential anomaly area, such as notifying a governmental agency of the violation, notifying a business (violator) that may be the cause of the air-pollution violation in the potential anomaly area, or the like, which are real-world actions that may be taken when detecting an air-pollution anomaly.

Thus, the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 5:
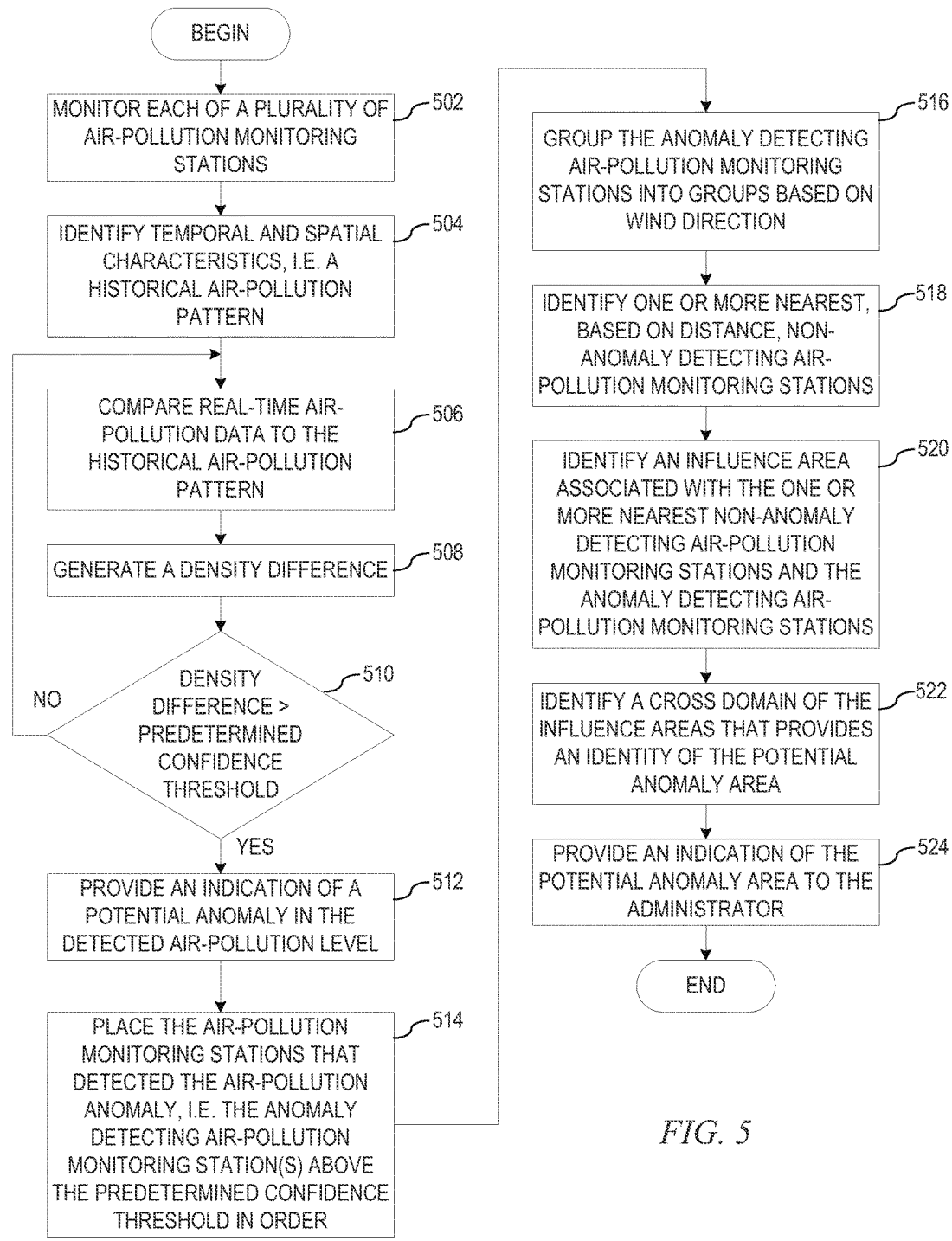
FIG. 5 depicts an exemplary operation performed by an air-pollution anomaly detection mechanism in detecting air-pollution anomalies in accordance with an illustrative embodiment.

FIG. 5 depicts an exemplary operation performed by an air-pollution anomaly detection mechanism in detecting air-pollution anomalies in accordance with an illustrative embodiment. As the operation begins, the air-pollution anomaly detection mechanism monitors each of a plurality of air-pollution monitoring stations (step 502) receiving real-time air-pollution data regarding the level of air pollution sensed by each monitoring station in the plurality of air-pollution monitoring stations. The air-pollution anomaly detection mechanism then identifies temporal and spatial characteristics, i.e. a historical air-pollution pattern, associated with each of the plurality of air-pollution monitoring stations (step 504).

For each of the plurality of air-pollution monitoring stations, the air-pollution anomaly detection mechanism compares real-time air-pollution data received from the air-pollution monitoring station for a given time to the temporal and spatial characteristics identified in the historical air-pollution pattern for the associated air-pollution monitoring station at the same time (step 506). Utilizing the comparison, the air-pollution anomaly detection mechanism generates a density difference that indicates a change in air-pollution identified by the air-pollution monitoring station (step 508). The air-pollution anomaly detection mechanism then determines whether the density difference is larger than a predetermined confidence threshold (step 510). If at step 510 the air-pollution anomaly detection mechanism determines that the density difference fails to exceed the predetermined confidence threshold, then the operation returns to step 506.

If at step 510 the air-pollution anomaly detection mechanism determines that the density difference exceeds the predetermined confidence threshold, then the air-pollution anomaly detection mechanism provides an indication of a potential anomaly in the detected air-pollution level to an administrator (step 512). Using the indication, the administrator may investigate the potential anomaly and, if there is an increase in air-pollution, take steps to decrease the air-pollution level, such as notifying a governmental agency of the violation, notifying a business (violator) that may be the cause of the air-pollution violation, or the like, which are real-world actions that may be taken when detecting an air-pollution anomaly.

In order to assist the administrator in identifying a potential violator, the air-pollution anomaly detection mechanism then places the air-pollution monitoring stations that detected the air-pollution anomaly, i.e. anomaly detecting air-pollution monitoring station(s), above the predetermined confidence threshold in order according to the determined density difference (step 514). Utilizing obtained wind direction data, the air-pollution anomaly detection mechanism groups the anomaly detecting air-pollution monitoring stations into groups based on wind direction (step 516). Within each group of anomaly detecting air-pollution monitoring stations, the air-pollution anomaly detection mechanism identifies one or more nearest, based on distance, non-anomaly detecting air-pollution monitoring stations to each of the anomaly detecting air-pollution monitoring stations (step 518). The air-pollution anomaly detection mechanism then identifies an influence area associated with the one or more nearest non-anomaly detecting air-pollution monitoring stations and the anomaly detecting air-pollution monitoring stations (step 520). The air-pollution anomaly detection mechanism then identifies a cross domain of the influence areas that provides an identity of the potential anomaly area (step 522). The air-pollution anomaly detection mechanism provides an indication of the potential anomaly area to the administrator (step 524), with the operation terminating thereafter. Using the potential anomaly area, the administrator may investigate the potential anomaly in the potential anomaly area and, if there is an increase in air-pollution may utilize the potential anomaly area to take steps to decrease the air-pollution level in that potential anomaly area, such as notifying a governmental agency of the violation, notifying a business (violator) that may be the cause of the air-pollution violation in the potential anomaly area, or the like, which are real-world actions that may be taken when detecting an air-pollution anomaly.

Figure 6:
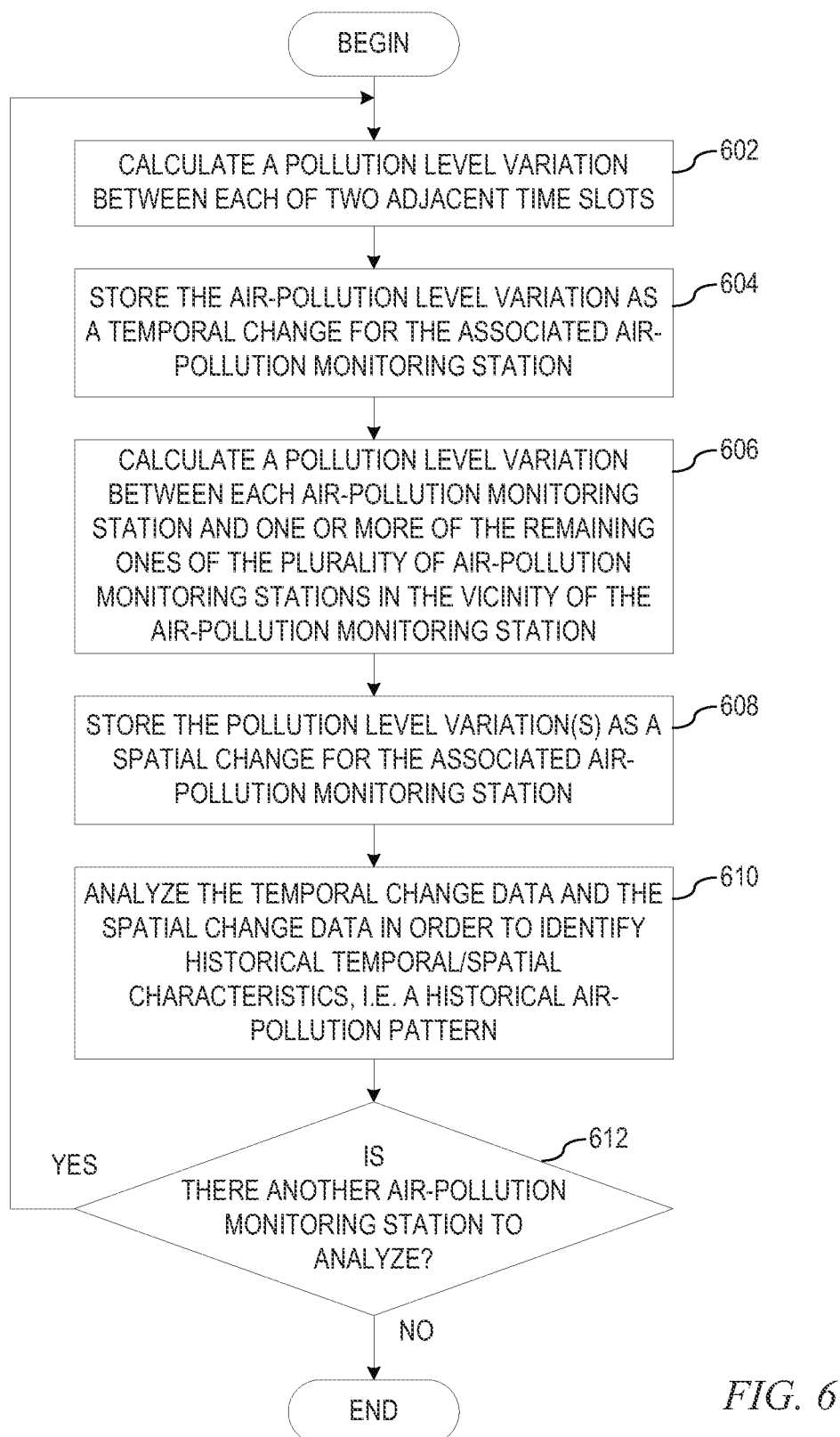
FIG. 6 depicts an exemplary operation performed by an air-pollution anomaly detection mechanism in identifying temporal and spatial characteristics associated with each of the plurality of air-pollution monitoring stations in accordance with an illustrative embodiment.

FIG. 6 depicts an exemplary operation performed by an air-pollution anomaly detection mechanism in identifying temporal and spatial characteristics associated with each of the plurality of air-pollution monitoring stations in accordance with an illustrative embodiment. As the operation begins, for each air-pollution monitoring station, the air-pollution anomaly detection mechanism uses real-time air-pollution data associated with the air-pollution monitoring station to calculate a pollution level variation between each of two adjacent time slots (step 602). For example, if at time $t_1$ an air-pollution monitoring station detects an air-pollution level of 3 and at time $t_2$ the same air-pollution monitoring station detects an air-pollution level of 4, then the air-pollution anomaly detection mechanism would calculate a temporal air-pollution level variation for the air-pollution monitoring station of positive 1 (+1). The air-pollution anomaly detection mechanism stores the air-pollution level variation as a temporal change for the associated air-pollution monitoring station in a temporal/spatial characteristics data structure (step 604).

The air-pollution anomaly detection mechanism also uses the real-time air-pollution data to calculate a pollution level variation between each air-pollution monitoring station and one or more of the remaining ones of the plurality of air-pollution monitoring stations within a predetermined distance of the air-pollution monitoring station (step 606). For example, if at time $t_1$ an air-pollution monitoring station detects an air-pollution level of 4 and, at the same time $t_1$, another air-pollution monitoring station detects an air-pollution level of 3, then the air-pollution anomaly detection mechanism would calculate a spatial air-pollution level variation of negative 1 (−1). The air-pollution anomaly detection mechanism stores the pollution level variation(s) as a spatial change for the associated air-pollution monitoring station in the temporal/spatial characteristics data structure (step 608).

Once temporal and spatial change data has been collected for the plurality of air-pollution monitoring stations, the air-pollution anomaly detection mechanism analyzes the temporal change data and the spatial change data in order to identify historical temporal/spatial characteristics, i.e. a historical air-pollution pattern, for each of the plurality of air-pollution monitoring stations (step 610). That is, the air-pollution anomaly detection mechanism utilizes the temporal change data to generate the historical air-pollution pattern for each of the plurality of air-pollution monitoring stations that shows changes in air-pollution levels over a given time period, such as a day, a week, a month, or the like. Further, using the spatial change data, the air-pollution anomaly detection mechanism generates the historical air-pollution pattern for each of the plurality of air-pollution monitoring stations that shows changes in air-pollution levels between air-pollution monitoring stations at different time periods. The air-pollution anomaly detection mechanism then determines if there is another air-pollution monitoring station to analyze (step 612).

If at step 612 the air-pollution anomaly detection mechanism determines that there is another air-pollution monitoring station, the operation returns to step 602. If at step 612 the air-pollution anomaly detection mechanism determines that there is not another air-pollution monitoring station, the operation terminates. The operation may be reinitiated, at periodic intervals, to analyze the historical temporal/spatial change data in relation to any newly collected temporal/spatial change data in order to update the historical air-pollution pattern for each of the plurality of air-pollution monitoring stations.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms that utilize a plurality of air-pollution monitoring stations in and/or around the sources of air pollution to detect air-pollution anomalies by comparing real-time monitoring data with analyzed temporal and spatial characteristic associated with the air-pollution monitoring stations. The mechanisms detect potential air-pollution anomalies by analyzing air-pollution temporal and spatial characteristics and then locating potential air-pollution anomalies according to weather conditions and correlations among nearby air-pollution monitoring stations. By detecting and locating potential pollution anomalies, environmental law enforcement agencies may be able to better trace and manage enterprise emission situation, so as to effectively prevent the illegal emission behavior of enterprises. Further, by detecting and locating potential pollution anomaly, the solutions/systems are provided for early identifications of pollution incidents and strengthening the environmental protection department of emergency response capability for emergence.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system, for detecting air-pollution anomalies, the method comprising:
   identifying, by temporal and spatial characteristic identification logic specifically configured by a processor in the data processing system, a historical air-pollution pattern for each of a plurality of air-pollution monitoring stations;
   for each of the plurality of air-pollution monitoring stations:
      responsive to receiving real-time air-pollution data from a particular air-pollution monitoring station, comparing, by anomaly detection logic specifically configured by the processor, the real-time air-pollution data to the historical air-pollution pattern associated with the particular air-pollution monitoring station;
      generating, by the anomaly detection logic, a density difference value based on the comparison of the real-time air-pollution data to the historical air-pollution pattern associated with the particular air-pollution monitoring station; and
      determining, by the anomaly detection logic, whether the density difference value is greater than a predetermined confidence threshold; and
   for each of a subset of the plurality of air-pollution monitoring stations whose associated density difference value is greater than the predetermined confidence threshold, generating, by the anomaly detection logic, an indication of an anomaly in detected air-pollution levels to an administrator, wherein the indication causes the administrator to perform one or more actions to remedy the anomaly in the detected air-pollution levels.

2. The method of claim 1, wherein the historical air-pollution pattern identifies temporal characteristics associated with the particular air-pollution monitoring station.

3. The method of claim 1, wherein the historical air-pollution pattern identifies spatial characteristics associated with the particular air-pollution monitoring station and one or more other air-pollution monitoring stations in the plurality of air-pollution monitoring stations.

4. The method of claim 1, further comprising:
   for each of the subset of the plurality of air-pollution monitoring stations whose associated density difference value is greater than the predetermined confidence threshold:
   identifying, by anomaly location identification logic specifically configured by the processor, a cross domain of the influence areas that provides an identity of a potential anomaly area; and
   generating, by the anomaly location identification logic, an indication of a potential anomaly area to the administrator, wherein the indication causes the administrator to perform one or more actions to remedy the anomaly in the detected air-pollution levels using the potential anomaly area.

5. The method of claim 4, wherein identifying the cross domain of the influence areas that provides the identity of the potential anomaly area comprises:
   placing, by the anomaly location identification logic, the subset of the plurality of air-pollution monitoring stations in order according to the determined density difference values;
   based on the order according to the determined density difference values and using an obtained wind direction data, grouping, by the anomaly location identification logic, the subset of the plurality of air-pollution monitoring stations one-by-one into groups based on the obtained wind direction data;
   identifying, by the anomaly location identification logic, one or more nearest, based on distance, non-detecting air-pollution monitoring stations to each of the subset of the plurality of air-pollution monitoring stations; and
   identifying, by the anomaly location identification logic, an influence area associated with each of the one or more nearest non-detecting air-pollution monitoring stations and the subset of the plurality of air-pollution monitoring stations.

6. The method of claim 5, wherein the groupings are limited based on a predetermined number of air-pollution monitoring stations.

7. The method of claim 1, wherein the historical air-pollution pattern is generated by the method comprising:
for each of the plurality of air-pollution monitoring stations:
calculating, by the temporal and spatial characteristic identification logic, a pollution level variation between each two adjacent time slots;
storing, by the temporal and spatial characteristic identification logic, each calculated air-pollution level variation between each two adjacent time slots as separate temporal change data for the associated air-pollution monitoring station;
calculating, by the temporal and spatial characteristic identification logic, a pollution level variation between each air-pollution monitoring station and one or more of the remaining ones of the plurality of air-pollution monitoring stations within a predetermined distance of the air-pollution monitoring station;
storing, by the temporal and spatial characteristic identification logic, each calculated pollution level variation between each air-pollution monitoring station and the one or more of the remaining ones of the plurality of air-pollution monitoring stations within a predetermined distance of the air-pollution monitoring station as separate spatial change data for the associated air-pollution monitoring station; and
analyzing, by the temporal and spatial characteristic identification logic, the temporal change data and the spatial change data in order to identify historical temporal/spatial characteristics thereby generating the historical air-pollution pattern.

8. A computer program product comprising a non-transitory computer readable storage medium having a computer readable program stored therein, wherein the computer readable program, when executed on a computing device, causes the computing device to:
identify, by temporal and spatial characteristic identification logic specifically configured by the computing device, a historical air-pollution pattern for each of a plurality of air-pollution monitoring stations;
for each of the plurality of air-pollution monitoring stations:
responsive to receiving real-time air-pollution data from a particular air-pollution monitoring station, compare, by anomaly detection logic specifically configured by the computing device, the real-time air-pollution data to the historical air-pollution pattern associated with the particular air-pollution monitoring station;
generate, by the anomaly detection logic, a density difference value based on the comparison of the real-time air-pollution data to the historical air-pollution pattern associated with the particular air-pollution monitoring station; and
determine, by the anomaly detection logic, whether the density difference value is greater than a predetermined confidence threshold; and
for each of a subset of the plurality of air-pollution monitoring stations whose associated density difference value is greater than the predetermined confidence threshold, generate, by the anomaly detection logic, an indication of an anomaly in detected air-pollution levels to an administrator, wherein the indication causes the administrator to perform one or more actions to remedy the anomaly in the detected air-pollution levels.

9. The computer program product of claim 8, wherein the historical air-pollution pattern identifies temporal characteristics associated with the particular air-pollution monitoring station.

10. The computer program product of claim 8, wherein the historical air-pollution pattern identifies spatial characteristics associated with the particular air-pollution monitoring station and one or more other air-pollution monitoring stations in the plurality of air-pollution monitoring stations.

11. The computer program product of claim 8, wherein the computer readable program further causes the computing device to:
for each of the subset of the plurality of air-pollution monitoring stations whose associated density difference value is greater than the predetermined confidence threshold:
identify, by anomaly location identification logic specifically configured by the computing device, a cross domain of the influence areas that provides an identity of a potential anomaly area; and
generate, by the anomaly location identification logic, an indication of a potential anomaly area to the administrator, wherein the indication causes the administrator to perform one or more actions to remedy the anomaly in the detected air-pollution levels using the potential anomaly area.

12. The computer program product of claim 11, wherein the computer readable program to identify the cross domain of the influence areas that provides the identity of the potential anomaly area further causes the computing device to:
place, by the anomaly location identification logic, the subset of the plurality of air-pollution monitoring stations in order according to the determined density difference values;
based on the order according to the determined density difference values and using an obtained wind direction data, group, by the anomaly location identification logic, the subset of the plurality of air-pollution monitoring stations one-by-one into groups based on the obtained wind direction data;
identify, by the anomaly location identification logic, one or more nearest, based on distance, non-detecting air-pollution monitoring stations to each of the subset of the plurality of air-pollution monitoring stations; and
identify, by the anomaly location identification logic, an influence area associated with each of the one or more nearest non-detecting air-pollution monitoring stations and the subset of the plurality of air-pollution monitoring stations.

13. The computer program product of claim 12, wherein the groupings are limited based on a predetermined number of air-pollution monitoring stations.

14. The computer program product of claim 8, wherein the historical air-pollution pattern is generated by the computer readable program further causing the computing device to:
for each of the plurality of air-pollution monitoring stations:
calculate, by the temporal and spatial characteristic identification logic, a pollution level variation between each two adjacent time slots;
store, by the temporal and spatial characteristic identification logic, each calculated air-pollution level variation between each two adjacent time slots as separate temporal change data for the associated air-pollution monitoring station;

calculate, by the temporal and spatial characteristic identification logic, a pollution level variation between each air-pollution monitoring station and one or more of the remaining ones of the plurality of air-pollution monitoring stations within a predetermined distance of the air-pollution monitoring station;

store, by the temporal and spatial characteristic identification logic, each calculated pollution level variation between each air-pollution monitoring station and the one or more of the remaining ones of the plurality of air-pollution monitoring stations within a predetermined distance of the air-pollution monitoring station as separate spatial change data for the associated air-pollution monitoring station; and analyze, by the temporal and spatial characteristic identification logic, the temporal change data and the spatial change data in order to identify historical temporal/spatial characteristics thereby generating the historical air-pollution pattern.

15. An apparatus comprising:

a processor; and a memory coupled to the processor, wherein the memory comprises instructions which, when executed by the processor, cause the processor to:

identify, by temporal and spatial characteristic identification logic specifically configured by the processor, a historical air-pollution pattern for each of a plurality of air-pollution monitoring stations;

for each of the plurality of air-pollution monitoring stations:

responsive to receiving real-time air-pollution data from a particular air-pollution monitoring station, compare, by anomaly detection logic specifically configured by the processor, the real-time air-pollution data to the historical air-pollution pattern associated with the particular air-pollution monitoring station;

generate, by the anomaly detection logic, a density difference value based on the comparison of the real-time air-pollution data to the historical air-pollution pattern associated with the particular air-pollution monitoring station; and determine, by the anomaly detection logic, whether the density difference value is greater than a predetermined confidence threshold; and for each of a subset of the plurality of air-pollution monitoring stations whose associated density difference value is greater than the predetermined confidence threshold, generate, by the anomaly detection logic, an indication of an anomaly in detected air-pollution levels to an administrator, wherein the indication causes the administrator to perform one or more actions to remedy the anomaly in the detected air-pollution levels.

16. The apparatus of claim 15, wherein the historical air-pollution pattern identifies temporal characteristics associated with the particular air-pollution monitoring station.

17. The apparatus of claim 15, wherein the historical air-pollution pattern identifies spatial characteristics associated with the particular air-pollution monitoring station and one or more other air-pollution monitoring stations in the plurality of air-pollution monitoring stations.

18. The apparatus of claim 15, wherein the instructions further cause the processor to:

for each of the subset of the plurality of air-pollution monitoring stations whose associated density difference value is greater than the predetermined confidence threshold:

identify, by anomaly location identification logic specifically configured by the processor, a cross domain of the influence areas that provides an identity of a potential anomaly area; and generate, by the anomaly location identification logic, an indication of a potential anomaly area to the administrator, wherein the indication causes the administrator to perform one or more actions to remedy the anomaly in the detected air-pollution levels using the potential anomaly area.

19. The apparatus of claim 18, wherein the instructions to identify the cross domain of the influence areas that provides the identity of the potential anomaly area further cause the processor to:

place, by the anomaly location identification logic, the subset of the plurality of air-pollution monitoring stations in order according to the determined density difference values;

based on the order according to the determined density difference values and using an obtained wind direction data, group, by the anomaly location identification logic, the subset of the plurality of air-pollution monitoring stations one-by-one into groups based on the obtained wind direction data;

identify, by the anomaly location identification logic, one or more nearest, based on distance, non-detecting air-pollution monitoring stations to each of the subset of the plurality of air-pollution monitoring stations; and identify, by the anomaly location identification logic, an influence area associated with each of the one or more nearest non-detecting air-pollution monitoring stations and the subset of the plurality of air-pollution monitoring stations.

20. The apparatus of claim 15, wherein the historical air-pollution pattern is generated by the instructions further causing the processor to:

for each of the plurality of air-pollution monitoring stations:

calculate, by the temporal and spatial characteristic identification logic, a pollution level variation between each two adjacent time slots;

store, by the temporal and spatial characteristic identification logic, each calculated air-pollution level variation between each two adjacent time slots as separate temporal change data for the associated air-pollution monitoring station;

calculate, by the temporal and spatial characteristic identification logic, a pollution level variation between each air-pollution monitoring station and one or more of the remaining ones of the plurality of air-pollution monitoring stations within a predetermined distance of the air-pollution monitoring station;

store, by the temporal and spatial characteristic identification logic, each calculated pollution level variation between each air-pollution monitoring station and the one or more of the remaining ones of the plurality of air-pollution monitoring stations within a predetermined distance of the air-pollution monitoring station as separate spatial change data for the associated air-pollution monitoring station; and analyze, by the temporal and spatial characteristic identification logic, the temporal change data and the spatial change data in order to identify historical temporal/ spatial characteristics thereby generating the historical air-pollution pattern.

\* \* \* \* \*